(12) United States Patent
Crouzen et al.

(10) Patent No.: US 6,570,379 B2
(45) Date of Patent: May 27, 2003

(54) METHOD FOR INSPECTING AN OBJECT OF ELECTRICALLY CONDUCTING MATERIAL

(75) Inventors: Paulus Carolus Nicolaas Crouzen, Amsterdam (NL); Mark Theodoor Looijer, Amsterdam (NL); Johan van der Steen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/932,189

(22) Filed: Aug. 17, 2001

(65) Prior Publication Data

US 2002/0093330 A1 Jul. 18, 2002

(30) Foreign Application Priority Data

Aug. 24, 2000 (EP) ............................................. 00307297

(51) Int. Cl.$^7$ ................................................ G01N 27/90
(52) U.S. Cl. ...................................... 324/240; 324/238
(58) Field of Search ................................ 324/220, 222, 324/240, 241, 242; 702/38, 199

(56) References Cited

U.S. PATENT DOCUMENTS

| | | | | |
|---|---|---|---|---|
| 3,361,960 A | * | 1/1968 | Renken, Jr. et al. | ......... 324/241 |
| 3,826,973 A | * | 7/1974 | Pflaum | ........................ 324/329 |
| 4,799,010 A | * | 1/1989 | Muller | ........................ 324/240 |
| 5,442,284 A | | 8/1995 | Kolditz | |
| 5,442,285 A | * | 8/1995 | Zombo et al. | ............... 324/227 |
| 5,485,084 A | | 1/1996 | Duncan et al. | |
| 5,602,474 A | | 2/1997 | Morrey, Jr. | |
| 6,037,768 A | * | 3/2000 | Moulder et al. | ............. 324/225 |
| 6,310,476 B1 | * | 10/2001 | Kawanami et al. | ......... 324/241 |

FOREIGN PATENT DOCUMENTS

EP 0321112 11/1988

OTHER PUBLICATIONS

European Search Report, examined by G. Kempf, dated Mar. 2, 2001.

* cited by examiner

*Primary Examiner*—Edward Lefkowitz
*Assistant Examiner*—Darrell Kinder

(57) ABSTRACT

A method of inspecting an electrically conductive object so as to detect the presence of an anomaly using a probe comprising a transmitter coil and a receiver coil, which method comprises the steps of:

(a) selecting a set of points on the near surface of the object that are to be inspected;
(b) selecting a first inspection point from the set;
(c) positioning the probe at the selected inspection point, inducing eddy currents in the object and determining a characteristic value, $\Phi$, of the electromagnetic field generated by the eddy currents;
(d) selecting a next inspection point from the set and repeating step (c) until all inspection points have had their turn; and
(e) inferring that an anomaly is present at an inspection point if the characteristic value $\Phi$ differs significantly from a norm.

7 Claims, 2 Drawing Sheets

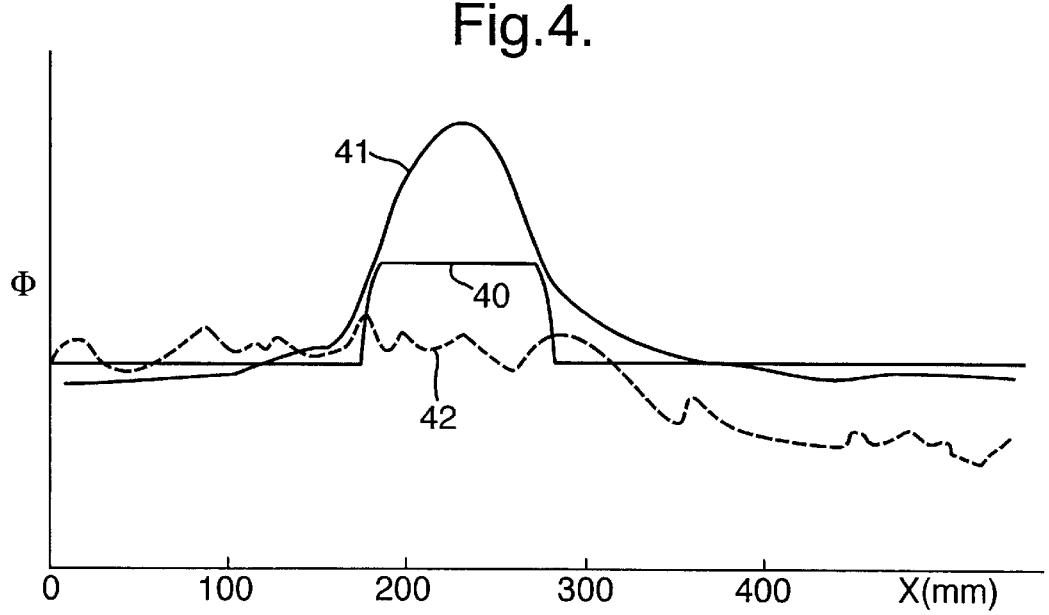

METHOD FOR INSPECTING AN OBJECT OF ELECTRICALLY CONDUCTING MATERIAL

BACKGROUND OF THE INVENTION

1. Field of the Invention

The present invention relates to a method of inspecting an electrically conductive object so as to detect the presence of an anomaly.

2. Description of Related Art

An anomaly can be a local decrease of the thickness of the object, which decrease is caused for example by corrosion.

European patent specification No. 321112 discloses a method of determining the thickness of a container wall means using a probe comprising a transmitter coil for inducing eddy currents in the object, and a receiver system for providing a signal indicative of changes in the strength of a magnetic field. The known method comprises inducing transient eddy currents in the object; receiving a signal indicative of the eddy current, and comparing the decay of the received signal over a period of time with a reference decay indicative of a known wall thickness, whereby the thickness of the container means wall portion can be inferred.

SUMMARY OF THE INVENTION

In the method according to the present invention, a probe is used, which comprises a transmitter coil for inducing eddy currents in the object, and a receiver system for providing a signal indicative of the strength of a magnetic field or changes in the strength of a magnetic field.

Examples of objects that can suitably be inspected with the method according to the present invention are metal plates or walls of container means, such as pipes, vessels or containers, having a radius of curvature that is larger than the thickness of the object. The electrically conducting material can be any electrically conducting material, for example carbon steel or stainless steel.

It is an object of the present invention to provide an improved method for inspecting an object so as to locate anomalies. It is a further object to provide an inspection method that is faster than the current inspection methods and which is less susceptible to variations in the electromagnetic properties of the object. A further object is to detect smaller anomalies than was possible with the known method.

To this end, the method of inspecting an electrically conductive object so as to detect the presence of an anomaly using a probe, which probe comprises a transmitter coil for inducing eddy currents in the object, and a receiver system for providing a signal indicative of the strength of a magnetic field or changes in the strength of a magnetic field, which receiver system includes at least one receiver, according to the present invention, comprises the steps of:

(a) selecting a set of points on the near surface of the object that are to be inspected;
(b) selecting a first inspection point from the set;
(c) positioning the probe at the selected inspection point, inducing transient eddy currents in the object and determining a characteristic value, $\Phi$, that relates to the amplitude of the signal of the receiver;
(d) selecting a next inspection point from the set and repeating step (c) until all inspection points have had their turn; and
(e) inferring that an anomaly is present at an inspection point if the characteristic value $\Phi$ differs significantly from a norm.

Suitably the probe contains at least two spaced apart receivers. Then step (c) comprises positioning the probe at the selected inspection point, inducing eddy currents in the object and determining a characteristic value, $\Phi$, that relates to the gradient of the electromagnetic field.

BRIEF DESCRIPTION OF THE DRAWINGS

The invention will now be described by way of example in more detail with reference to the accompanying drawings, wherein

FIG. 4 shows a diagram indicating the lift-off as a function of the position along an object.

DESCRIPTION OF THE PREFERRED EMBODIMENTS

Figure 1:
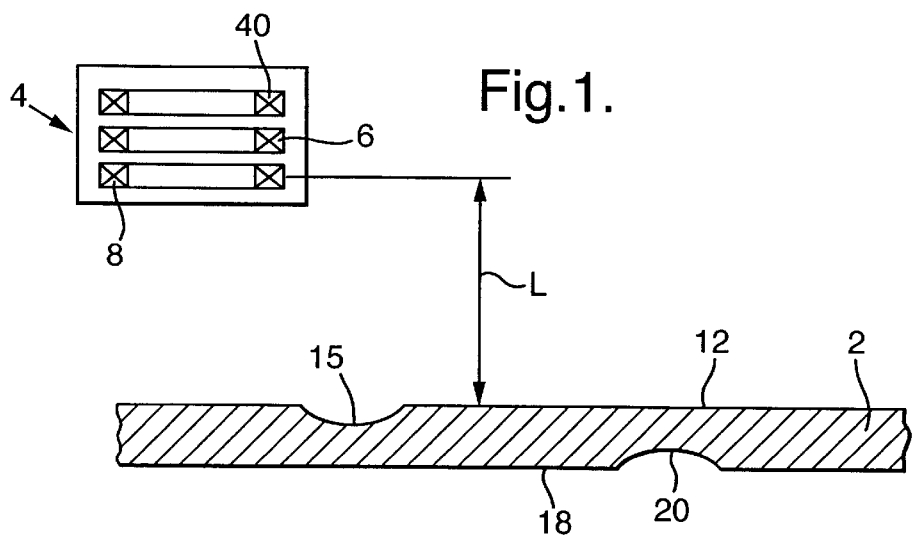
FIG. 1 shows a first embodiment of the invention.

Reference is now made to FIG. 1. The object of electrically conducting material is referred to with reference numeral 2 and the probe is referred to with reference numeral 4. The probe 4 comprises a transmitter coil 6 for transmitting an electromagnetic field and a receiver 8.

The transmitter coil 6 is connected to a device (not shown) for energizing the transmitter coil and the receiver system is connected to a device (not shown) for recording the signals from the receiver system.

The distance between the probe 4 and the near surface 12 is denoted by L, and the space between the probe 4 and the object 2 is for example filled with an insulation layer (not shown) covering the near surface 12. The distance L is also called lift-off.

The object 2 has been provided with two anomalies: one at the near surface 12, referred to with reference numeral 15, and a second anomaly at the far surface 18, referred to with reference numeral 20.

During normal operation the probe 4 is moved along the near surface 12 at a distance L therefrom, and at a number of points a detection is made.

To make a detection, the probe 4 is positioned at the first point of the set of points. Eddy currents are induced in the object by activating the transmitter coil 6 and a characteristic value, $\Phi$, of the electromagnetic field generated by the eddy currents is determined. Then the probe 4 is positioned at a next point and eddy currents are induced in the object and a characteristic value, $\Phi$, of the electromagnetic field generated by the eddy currents is determined. This procedure is repeated until all points have had their turn.

Then it is inferred that an anomaly is present at an inspection point if the characteristic value $\Phi$ differs significantly from a norm.

Figure 2:
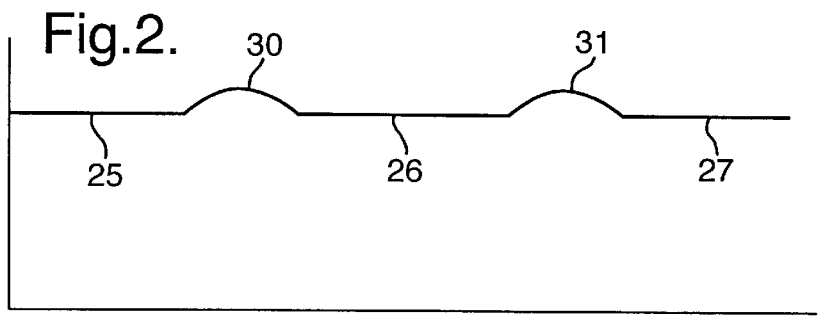
FIG. 2 shows a recording of the characteristic value as a function of the position of the probe.

FIG. 2 shows a diagram of the characteristic value as a function of the position probe 4 along the object 2. The characteristic value is constant in the absence of an anomaly, see lines segments 25, 26 and 27. The anomalies 15 and 20 can be found on the curve at 30 and 31.

In order to induce transient eddy currents in the object, the transmitter coil 6 is energized and abruptly de-energized.

The characteristic value is determined by making a recording V(t) of the signal of the receiver and determining the average amplitude $$\overline{V} = (1/n)\sum_{i=1}^{n} V(t_0 + (i-1)\Delta),$$

wherein $t_0$ is an initial time, $\Delta$ is the sample interval and n is the number of samples that are included in the summation.

Suitably, the probe 4 contains a second receiver 40, which is spaced apart from the first one 8. The distance between the receivers 40 and 8 is of the order of the lift-off, and suitably between 0.1 and 0.9 times the lift-off. In this case, for transient eddy currents, determining the characteristic value comprises the steps of recording the signals of the receivers with time, wherein $V_1(t)$ is the signal of the first receiver 8 with time (t) and $V_u(t)$ is the signal of the second receiver 40 with time (t), and determining the characteristic value $$\Phi = \frac{\sum_{i=1}^{n} V_u(t_0 + (i-1)\Delta)}{\sum_{i=1}^{n} V_l(t_0 + (i-1)\Delta)},$$

wherein $t_0$ is an initial time, $\Delta$ is the sample interval and n is the number of samples that are included in the summation.

Figure 3A:
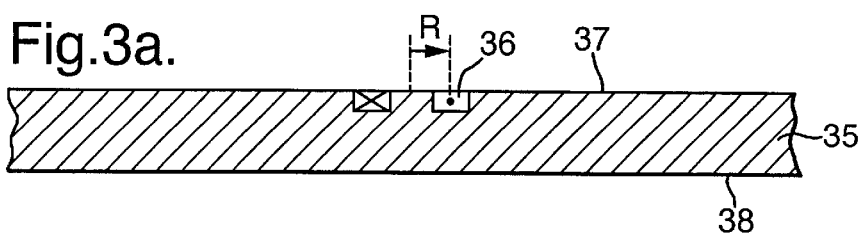
FIG. 3a shows schematically the eddy currents generated in an object without an anomaly.
Figure 3B:
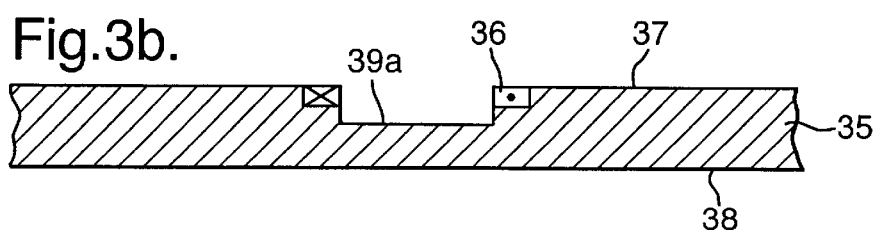
FIG. 3b shows schematically the eddy currents generated in an object with a small anomaly.
Figure 3C:
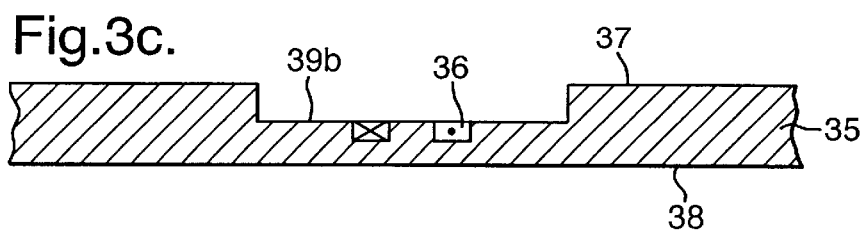
FIG. 3c shows schematically the eddy currents generated in an object with a larger anomaly.

In order to explain why the method according to the present invention is capable of detecting small anomalies (or defects), reference is now made to FIGS. 3a–3c. FIGS. 3a–3c show the eddy currents generated in an object 35. For the sake of simplicity only one eddy current 36 is shown. Eddy current 36 circulates in a plane parallel to the near surface 37 of the object 35, the cross means that the eddy current runs into the plane of drawing and the point means that the eddy current comes out of the plane of drawing. When the characteristic value is determined during the test, the eddy current diffuses towards the far surface 38 and its magnitude decreases. Known methods rely on the time it takes the eddy currents to reach the far surface 38, whereas the method according to the present invention relies on the characteristic value, $\Phi$. The characteristic value, $\Phi$, is a function of the lift-off L and the radius of the eddy currents R.

FIG. 3a shows the object 35 without an anomaly. Both methods will give the same result. FIG. 3b shows the object 35 with a small defect 39a. With the same probe configuration (not shown) and lift-off eddy currents 36 are generated that are arranged around the small anomaly 39a. The eddy-currents 36 start at the near surface 37, and therefore a method that relies on the time it takes the eddy currents to reach the far surface 38 will not detect the anomaly 39a. However, because the characteristic value, $\Phi$, depends on the radius, the method according to the present invention does detect the anomaly 39a. For the sake of completeness, for a relatively large anomaly 39b shown in FIG. 3c, the method relying on the time it takes the eddy currents to reach the far surface 38 will give a decreased thickness, whereas the method according to the present invention will give an increased lift-off.

In order to illustrate the result of the method of the present invention, reference is now made to FIG. 4, which shows the characteristic value $\Phi$ in arbitrary units as a function of the position X of the probe along an object. Curve 40 shows the actual defect profile, which is the lift-off that is to be expected when a probe passes at a distance of 50 mm over a flat object having a nominal thickness of 15 mm provided with a 2 mm deep defect at the near surface. Whereas curve 41 shows the characteristic value as a function of the position. The characteristic value had been determined with a probe comprising two receiver coils and with times between 6 and 40 ms.

The defect is clearly visible. For a comparison, the thickness of the object had been determined using a conventional pulsed eddy-current technique, wherein the time in which the eddy-currents diffuse to the far surface is used to determine the wall thickness. Dashed line 42 is the thickness in arbitrary units as a function of the position, and it can be seen that the anomaly is not detected. From FIG. 4 it can be concluded that the characteristic value is a measure for the lift-off for a flat and undisturbed object, however, an anomaly causes a change in the characteristic value that is larger than the true lift-off.

For detecting an anomaly at the near surface, the method according to the present invention is quick, because the first milliseconds of the received signal contains sufficient information to detect the anomaly at the near surface. In contrast thereto, the known methods require the eddy currents to diffuse to the far side of the surface, which takes about 40 to 100 milliseconds. Therefore a known method requires at least 40 to 100 milliseconds before a defect can be detected.

It will be understood that this advantage of the present invention is lost when the anomalies that have to be detected are at the far surface, because they will only be detected when the eddy-currents have diffused to the far surface. This has been experimentally verified.

In the embodiment of the probe 4 as shown in FIG. 1, the receivers 8 and 40 are located one above the other in a vertical direction—perpendicular to the near surface 12 of the object 2. In an alternative embodiment (not shown) the receiver antenna means are spaced apart in a horizontal direction—parallel to the near surface 12. This is particularly useful, when a U-shaped ferrite core is used of which the open end points towards the object. The U-shaped ferrite core contains on both legs a transmitter coil and a receiver coil, then a second receiver coil is arranged next to the U-shaped ferrite core.

Because corrosion under insulation occurs at the near surface, the present invention can very suitably be used for inspection of corrosion under insulation. Not only does using the first milliseconds of the signal filter out effects of the far surface, but it also makes the method very fast. With a conventional eddy-current method about 20 m/hour can be inspected, whereas the method of the present invention allows inspection rates of more than 100 m/hour.

There is another advantage of the method according to the present invention compared with the conventional methods. A conventional eddy current method relies on measuring the time it takes the eddy currents to reach the far surface. The wall thickness is a product of this time and the velocity at which the eddy currents travel through the material. The latter velocity depends on the electrical conductivity and magnetic permeability of the material. These properties are dependent on the temperature of the sample and, for ferromagnetic materials such as carbon steel, on the micro structure of the material. The electrical conductivity and magnetic permeability are often found to change significantly from one position to the next on carbon steel materials. As a result, the velocity at which the eddy currents travel through the material changes from one position to the next on a carbon steel specimen. This introduces a variation in the aforementioned time which conventional pulsed eddy current methods can not distinguish from variations due to changes in the wall thickness. This phenomenon limits the reliability of conventional methods when applied to carbon steel objects. Variations in the velocity at which the eddy currents travel through the material are not relevant for the method of the present invention. The method of the present invention is therefore more suitable for application to a carbon steel test specimen than a conventional method.

Corrosion under insulation takes place at pipes covered with insulation material. The insulation material is usually protected against rain by a metal cover. This metal cover is referred to as "jacket". The jacket is often made of aluminum or steel and is about 0.7 mm thick. The jacket is applied in sections with a typical length of 1 m. Ingress of water is prevented by partial overlapping of two jacket sections. The jacket does not need to be removed during inspection with eddy current techniques. To a first approximation, the effect of the jacket is a delay of $\Delta t$ in the received signal: if the signal is s(t) without jacket, it will be about s(t-$\Delta t$) in the signal with jacket. The magnitude of $\Delta t$ varies along the jacket section: near the jacket overlap $\Delta t$ is larger compared to the value in the middle. Variations in the shift $\Delta t$ affect conventional pulsed eddy current methods: variation in $\Delta t$ appears as spurious variations in the measured thickness of the steel. Applicant had found that the method of the present invention, when two receivers are used, is less sensitive to the presence of a metal jacket. A reason is that the characteristic value $\Phi$ was experimentally found to be nearly independent of
the time t: $\Phi((t) \approx \Phi(t-\Delta t)$, wherein $$\Phi(\tau) = \frac{\sum_{i=1}^{n} V_u(\tau + (i-1)\Delta)}{\sum_{i=1}^{n} V_l(\tau + (i-1)\Delta)},$$

in
which latter equation $\tau=t$ or $\tau=t-\Delta t$.

In the specification and in the claims the word norm is used, this is the expected magnitude of the characteristic value in the absence of an anomaly.

In the specification and in the claims, a significant difference is a statistically significant difference, for example more than the standard deviation.

The receivers discussed with reference to the drawings are coils, and the signal from the receiver represents the change of the strength of the magnetic field with time. Alternatively, the receivers can be Hall effect transducers. When the receivers are Hall effect transducers, or when the signals from the coils are integrated, the signals are indicative of the strength of the magnetic field.

In case the receivers are coils, the diameter is suitably of the order of the lift-off, and more suitably between 0.1 and 0.9 times the lift-off.

The receivers 8 and 40 are located one above the other in a vertical direction—perpendicular to the near surface 12 of the object 2. In an alternative embodiment (not shown) the receiver antenna means are spaced apart in a horizontal direction—parallel to the near surface 12. This is particularly useful when a U-shaped ferrite core is used of which the open end points towards the object. The U-shaped ferrite core contains on both legs a transmitter coil and a receiver coil, then a second receiver coil is arranged next to the U-shaped ferrite core.

What is claimed is:

1. A method of inspecting an electrically conductive object so as to detect the presence of an anomaly using a probe, which probe comprises a transmitter coil for inducing eddy currents in the object, and a receiver system for providing a signal indicative of the strength of a magnetic field or changes in the strength of a magnetic field, which receiver system includes at least one receiver, which method comprises the steps of:

(a) selecting on the surface of the object, which surface is nearest to the probe, a set of points that are to be inspected;

(b) selecting a first inspection point from the set;

(c) positioning the probe at the selected inspection point, inducing transient eddy currents in the object and determining a characteristic value, $\Phi$ that relates to the amplitude of the signal of the receiver before the eddy currents have diffused to the far surface of the object, thereby being a function of the lift-off and the radius of the eddy currents;

(d) selecting a next inspection point from the set and repeating step (c) until all inspection points have had their turn; and (e) inferring that an anomaly is present at an inspection point if the characteristic value $\Phi$, differs significantly from a norm.

2. The method according to claim 1, wherein the receiver system consists of a single receiver, wherein determining the characteristic value comprises making a recording V(t) of the signal of the receiver and determining the characteristic value as the average amplitude $$\overline{V} = (1/n) \sum_{i=1}^{n} V(t_0 + (i-1)\Delta),$$

wherein $t_0$ is an initial time, $\Delta$ is the sample interval and n is the number of samples that are included in the summation.

3. The method according to claim 2, wherein the receiver system comprises a receiver coil, and wherein the signal represents the change of the eddy current, and wherein V is the voltage at the terminals of the receiver coil.

4. A method of inspecting an electrically conductive object so as to detect the presence of an anomaly using a probe, which probe comprises a transmitter coil for inducing eddy currents in the object, and a receiver system for providing a signal indicative of the strength of a magnetic field or changes in the strength of a magnetic field, which receiver system includes at least two spaced apart receivers, which method comprises the steps of:

(a) selecting on the surface of the object, which surface is nearest to the probe, a set of points that are to be inspected;

(b) selecting a first inspection point from the set;

(c) positioning the probe at the selected inspection point, inducing transient eddy currents in the object and determining a characteristic value, $\Phi$, that relates to the gradient of the electromagnetic field generated by the eddy currents, thereby being a function of the lift-off and of the radius of the eddy currents;

(d) selecting a next inspection point from the set and repeating step (c) until all inspection points have had their turn; and (e) inferring that an anomaly is present at an inspection point if the characteristic value $\Phi$ differs significantly from a norm.

5. The method according to claim 4, wherein inducing eddy currents in the object includes inducing transient eddy currents in the object, and wherein determining the characteristic value comprises the steps of recording the signals of the receivers with time, wherein $V_u(t)$ is the signal of the first receiver with time (t) and $V_1(t)$ is the signal of the second receiver with time (t), and determining the characteristic value $$\Phi = \frac{\sum_{i=1}^{n} V_u(t_0 + (i-1)\Delta)}{\sum_{i=1}^{n} V_l(t_0 + (i-1)\Delta)},$$

wherein $t_0$ is an initial time, $\Delta$ is the sample interval and n is the number of samples that are included in the summation.

6. The method according to claim 4 wherein the receiver system comprises a first receiver coil and a second receiver coil that is spaced apart from the first receiver coil, and wherein each signal represents the change of the eddy current, and wherein $V_u$ and $V_1$ are the voltages at the terminals of the first and second receiver coil, respectively.

7. The method according to claim 5 wherein the receiver system comprises a first receiver coil and a second receiver coil that is spaced apart from the first receiver coil, and wherein each signal represents the change of the eddy current, and wherein $V_u$ and $V_1$ are the voltages at the terminals of the first and second receiver coil, respectively.

* * * * *